United States Patent
Hall et al.

(10) Patent No.: US 11,353,469 B2
(45) Date of Patent: Jun. 7, 2022

(54) NONTOXIC COMPOUNDS FOR USE AS TAGGANTS IN NUTRITIONAL AND PHARMACEUTICAL PRODUCTS

(71) Applicant: Hall Labs, LLC, Provo, UT (US)

(72) Inventors: David R Hall, Provo, UT (US); Steven J. M. Butala, Provo, UT (US)

(73) Assignee: Hall Labs LLC, Provo, UT (US)

( * ) Notice: Subject to any disclaimer, the term of this patent is extended or adjusted under 35 U.S.C. 154(b) by 88 days.

(21) Appl. No.: 16/432,898

(22) Filed: Jun. 5, 2019

(65) Prior Publication Data

US 2020/0386775 A1    Dec. 10, 2020

(51) Int. Cl.
| | |
|---|---|
| *G01N 33/94* | (2006.01) |
| *G01N 33/493* | (2006.01) |
| *G01N 33/52* | (2006.01) |
| *G01N 33/58* | (2006.01) |
| *G01N 33/497* | (2006.01) |
| *G01N 33/15* | (2006.01) |

(52) U.S. Cl.
CPC ............ *G01N 33/94* (2013.01); *G01N 33/15* (2013.01); *G01N 33/493* (2013.01); *G01N 33/497* (2013.01); *G01N 33/52* (2013.01); *G01N 33/58* (2013.01)

(58) Field of Classification Search
CPC ...... G01N 33/94; G01N 33/15; G01N 33/493; G01N 33/497; G01N 33/52; G01N 33/58; G01N 2560/00
See application file for complete search history.

(56) References Cited

U.S. PATENT DOCUMENTS

| | | | | |
|---|---|---|---|---|
| 4,981,144 A | * | 1/1991 | Carels, Jr. .......... | A61B 5/14507 141/237 |
| 2004/0037879 A1 | * | 2/2004 | Adusumilli .......... | A61K 9/5084 424/468 |
| 2007/0142739 A1 | * | 6/2007 | Sonnenberg ......... | G01N 33/497 600/532 |

FOREIGN PATENT DOCUMENTS

WO    WO-2018162513 A1 *   9/2018    ............. G01N 33/48

OTHER PUBLICATIONS

Suarez, F., et al. "Differentiation of mouth versus gut as site of origin of odoriferous breath gases after garlic ingestion." American Journal of Physiology—Gastrointestinal and Liver Physiology 276.2 (1999): G425-G430. (Year: 1999).*

(Continued)

*Primary Examiner* — Jennifer Wecker
*Assistant Examiner* — Oyeleye Alexander Alabi

(57) ABSTRACT

The method of confirming consumption of a tagged pharmaceutical or nutritional product includes the step of providing a subject with a pharmaceutical or nutritional product which has been tagged with a safe, for example, a plant-based, compound. These compounds may include asparagusic acid or a derivative thereof which is found in asparagus, garlic or an extract of garlic, or 1,8-cineole. Alternatively, the taggant may be dimethylsulfoxide. A subject may be provided with and instructed to consume the tagged product according to a defined protocol. A sample of bodily waste or other biological sample may be collected from the subject and analyzed for the presence of the tag or a metabolite thereof. This method may be used to confirm compliance with the protocol in clinical drug trials or nutritional studies.

22 Claims, 3 Drawing Sheets

(56) References Cited

OTHER PUBLICATIONS

Gallicano, Keith, Brian Foster, and Shurjeel Choudhri. "Effect of short-term administration of garlic supplements on single-dose ritonavir pharmacokinetics in healthy volunteers." British journal of clinical pharmacology 55.2 (2003): 199-202. (Year: 2003).*

* cited by examiner

Asparagusic Acid 1,8-Cineole

Allyl Methyl Sulfide

US 11,353,469 B2

NONTOXIC COMPOUNDS FOR USE AS TAGGANTS IN NUTRITIONAL AND PHARMACEUTICAL PRODUCTS

TECHNICAL FIELD

This disclosure relates to compounds which may be used to tag and track consumption of nutritional and pharmaceutical products.

BACKGROUND

It is often useful or even necessary to track consumption of a nutritional or pharmaceutical product. However, developing a unique method of detecting each different product is inefficient, costly, and cumbersome. By adding a taggant to product, a single method of detecting the taggant can be used to track consumption of a variety of products and use a single analytical technique.

In an example, a source of monetary loss and inefficiency in clinical trials is noncompliance. Subjects in the trials often fail to consume the study drug according to the prescribed dosing schedule or may not even consume the study drug at all. By using taggants, clinical trial data could be analyzed with accurate information about whether the subject properly complied with the study protocol.

In another example, food products from a particular source may need to be tracked. This may be done to confirm the source of the food or be part of a protocol for conducting nutritional studies.

Taggants used for this purpose are preferably safe for consumption and preferably detectable in human waste or other biological samples. Components isolated from edible plant material are examples of taggants that may meet these criteria. Taggant compounds which are safe and easily detectable, for example, in bodily waste, are needed.

SUMMARY

We disclose a method of tagging pharmaceutical and nutritional products using safe compounds which may be detected in biological samples directly or their metabolites or derivatives may be detected in biological samples.

The method includes the step of mixing the taggant with the pharmaceutical and nutritional product or applying the taggant to the pharmaceutical and nutritional product. In some embodiments, the pharmaceutical or nutritional product may be encased in a capsule, the capsule being impregnated with taggant. The tagged pharmaceutical and nutritional product (hereinafter "tagged product") may be provided to a subject and the subject may be instructed to consume the tagged product. The instructions may be to consume the tagged product according to a variety of methods known in the art, including consuming it orally or applying it topically.

A biological sample may then be collected from the subject for analysis to detect the taggant or metabolites of the taggant. The biological sample may be a urine sample, a sample of exhaled breath, or other samples referenced herein.

The biological sample may be analyzed using an appropriate technique to detect the presence of the taggant or metabolites of the taggant, thereby confirming consumption of the tagged product. Absence of the taggant or metabolites of the taggant may indicate lack of consumption of the tagged product.

Examples of taggants derived from plants include asparagusic acid, garlic or extracts thereof, and 1,8-cineole. Another example of a taggant is dimethylsulfoxide.

Examples of techniques which may be used to analyze the biological sample include head space gas chromatography-mass spectrometry, head space gas chromatography-differential mobility spectrometry, gas chromatography-mass spectrometry, gas chromatography-differential mobility spectrometry, liquid chromatography with tandem mass spectrometry, and electronic nose analysis.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
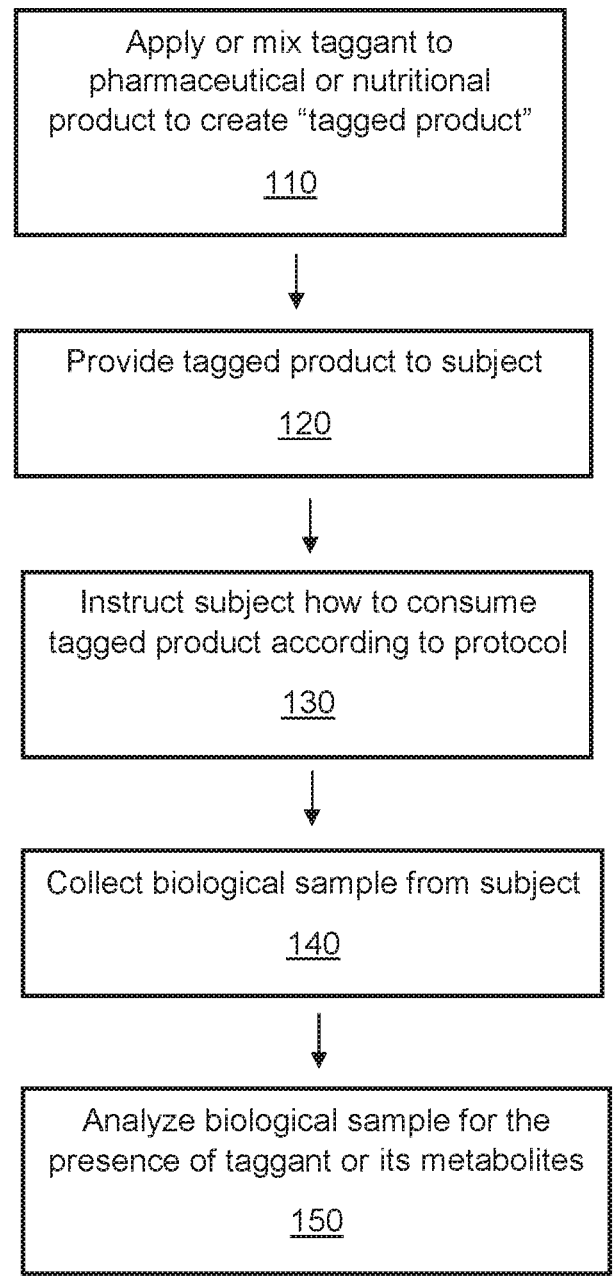
FIG. 1 is a flow chart which illustrates an embodiment of a method of using the taggants as disclosed herein.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a method of tagging pharmaceutical and nutritional products using one or more taggants which are safe for consumption and detectable in biological samples, including bodily waste. The taggant may be mixed with the pharmaceutical or nutritional product during product manufacture. Alternatively, the taggant may be sprayed, painted, or otherwise applied to the surface of the pharmaceutical or nutritional product.

In some embodiments, the pharmaceutical or nutritional product may be provided within a capsule, for example, a gelatin capsule. The taggant may be placed within the capsule between an inner surface and an outer surface of the capsule. In one embodiment, the inner surface and the outer surface may be constructed of the material from which the remainder of the capsule is constructed, for example, gelatin. In another embodiment, the inner surface and the outer surface made of an inert coating. The inner surface of the capsule may provide an inner barrier between the taggant and the pharmaceutical or nutritional product within the capsule. This inner barrier may prevent undesired interaction between the taggant and the pharmaceutical or nutritional product which could damage the taggant, the pharmaceutical or nutritional product, or both. The outer surface of the capsule may provide an outer barrier between the taggant and the environment outside the capsule. This outer barrier may prevent undesired interaction between the taggant and the environment which could damage the taggant.

The tagged pharmaceutical or nutritional product (hereinafter, "tagged product") may be provided to a subject and the subject may be instructed to consume the tagged product. The instructions may be to consume the tagged product orally, intranasally, intramuscularly, sublingually, by applying topically, or any other method of administration known in the art.

Subsequently, a biological sample may be collected from the subject. The biological sample may be saliva, exhaled breath, hair, urine, feces, or any other sample which may be collected and assayed for the presence of a taggant or a metabolite of a taggant. In some embodiments, the biological sample is urine. In some embodiments, the urine sample may be collected as a spot urine sample or a first morning void urine sample. In other embodiments, the urine sample may be a 24-hour urine sample. In another embodiment, the subject may exhale into a device which may analyze the subjects exhaled breathe for volatile organic compounds (hereinafter, "VOCs") as described elsewhere herein.

In some embodiments, the taggants may be derived from plant material, for example, plants commonly used as a food source. The taggant may, therefore, be known for its safety for consumption, particularly in small amounts which may be used for purposes of preparing the tagged products.

In one example, the taggant may be asparagusic acid or a derivative thereof. Asparagusic acid and its metabolites and derivatives are sulfur-containing compounds found in asparagus. These compounds may be responsible for causing the odor of urine that may be present after consuming asparagus. Typically, 200 g of asparagus contains at least enough asparagusic acid to detect in the headspace above a volume of urine collected from an individual who has consumed the asparagus.

Urine which includes asparagusic acid and/or its metabolites or derivatives may be detected by sampling and analyzing the VOCs in the headspace of a urine sample collected from a subject who has consumed the asparagusic acid taggant. In some examples, VOCs including asparagusic acid and/or its metabolites may be detected using at least one of the following list: head space gas chromatography-mass spectrometry, head space gas chromatography-differential mobility spectrometry, and electronic nose analysis. Electronic noses may include sensors selected from one or more of the following: metal-oxide-semiconductors, conducting polymers, polymer composites, quartz crystal microbalance, and surface acoustic wave. In an example, the electronic nose may be the Cyranose 320 developed by Cyrano Sciences, Pasadena, Calif., U.S.A. and manufactured by Sensigent, LLC. The Cyranose 320 includes a plurality of semi-selective sensors and electronic computation.

In another example, the taggant may be garlic or an extract thereof. The primary metabolite of garlic is allyl methyl sulfide. In an example, breath analysis may be used to detect the presence of allyl methyl sulfide. Peak detection in exhaled breath may occur within 2-3 hours of consumption of the garlic taggant. Gas-chromatography-mass spectrometry, gas chromatography-differential mobility spectrometry, or electronic nose may be used to detect ally methyl sulfide in exhaled breath. In another example, allyl methyl sulfide may be detected in the head space of a urine sample. In an example, urine may be collected between two and four hours after consumption of the garlic taggant. The headspace of urine may be analyzed using one or more of the following list: head space gas chromatography-mass spectrometry, head space gas chromatography-differential mobility spectrometry, and electronic nose analysis.

In another example, the taggant may be 1,8-cineole, also known as eucalyptol, 1,8-cineol, cajeputol, 1,8-epoxy-p-menthane, 1,8-oxido-p-menthane, eucalyptol, eucalyptole, 1,3,3-trimethyl-2-oxabicyclo[2,2,2]octane, cineol, and cineole. The metabolite of 1,8-cineole typically produced in the highest concentration is 2-hydroxycineole. In an example, 2-hydroxycineole or other metabolites of 1,8-cineole may be detected in the headspace of a urine sample using liquid chromatography with tandem mass spectrometry.

In another example, the taggant may be dimethylsulfoxide (hereinafter, "DMSO"). A tagged product comprising DMSO may be administered orally or applied topically. A single dose of 1 g/kg body weight of DMSO has been shown to be recoverable in in urine in amounts that range from 30-68% when DMSO is administered orally and 13% when DMSO is applied topically. Furthermore, when orally administered the compound could be detected in urine 30 minutes after administration with peak excretion seen within approximately 4 hours. When applied topically, DMSO has been detected in urine 2 hours of administration. After oral administration of DMSO, one of its metabolites, dimethylsulfide (DMS), may be detected on the exhaled breath of subjects utilizing gas chromatography-mass spectrometry, gas chromatography-differential mobility spectrometry, or electronic nose techniques. The headspace of urine samples may be analyzed to detect DMSO using one or more of the following techniques: head space gas chromatography-mass spectrometry, head space gas chromatography-differential mobility spectrometry, and electronic nose analysis with a specific focus for DMSO detection.

In some embodiments, the analytical devices used to detect the taggant or metabolites thereof is part of a toilet. The user may deposit the biological sample, for example, urine, into the toilet which may include a sample capture device. The sample capture device may divert the biological sample into one of the analytical devices disclosed herein to detect the presence of the taggant or metabolite thereof.

Referring now to the drawings, FIG. 1 provides a flow chart which illustrates an embodiment of the disclosed method. In step 110, taggants are applied to the surface of pharmaceutical or nutritional product or mixed with the pharmaceutical or nutritional product. This step results in the "tagged product." In step 120, the tagged product is provided to a subject. The subject is provided with instruction as to how to consume the product according to a protocol (step 130). This may include timing of consumption, method of consumption, and other information, for example, whether the tagged product should be consumed with food. After a sufficient amount of time, for example, an amount of time required for the tagged product to be metabolized by the subject's body, a biological sample is collected from the subject (step 140). The biological sample may be urine, blood, saliva, or other biological materials discussed herein. In step 150, the biological sample is analyzed using one of the analytical methods discussed herein to detect the presence (or absence) of the taggant or a metabolite of the taggant. The subject's compliance with the protocol explained to the subject in step 130 may be assessed according to the results of the analysis.

Figure 2:
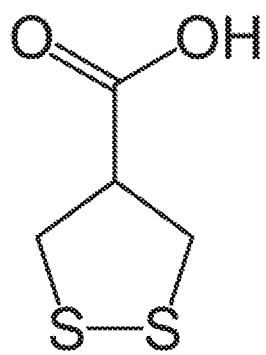
FIG. 2 illustrates the chemical structures of taggants disclosed herein.
Figure 2:
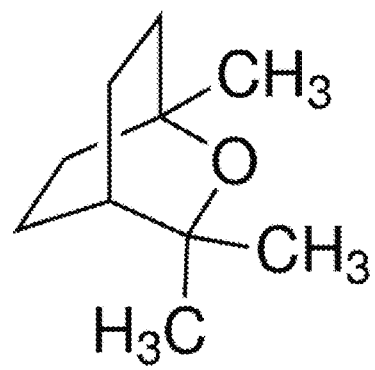
Figure 2:

FIG. 2 provides the chemical structures of asparagusic acid and 1,8-cineole which are disclosed herein as examples of taggants which may be used according to embodiments of the disclosed method. FIG. 2 also illustrates the structure of allyl methyl sulfide which is a metabolite of components found in garlic. By using garlic extract as a taggant, the collected biological sample may be analyzed for the presence or absence of allyl methyl sulfide to assess the subject's compliance with the protocol.

Figure 3:
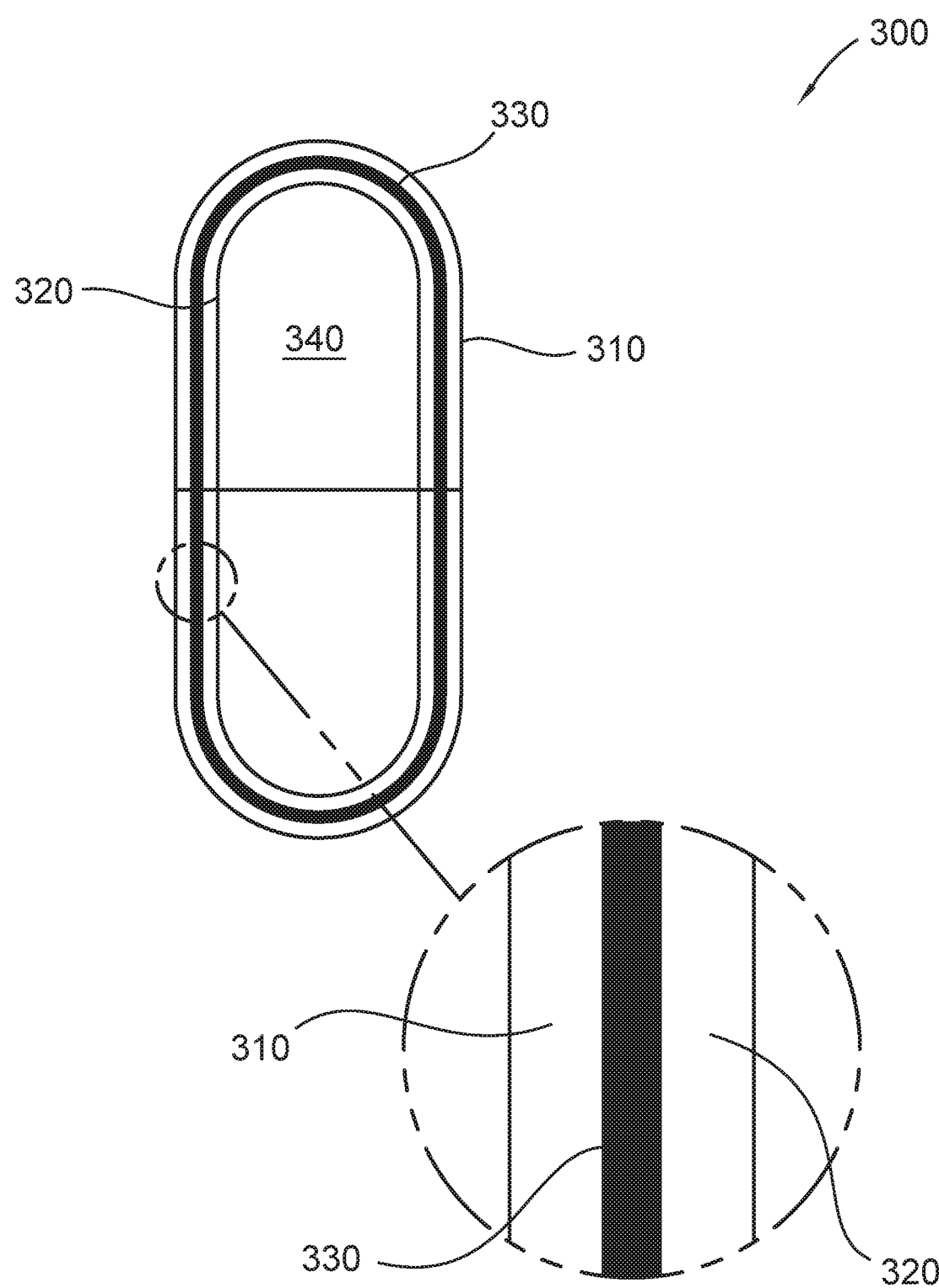
FIG. 3 is a schematic drawing of a capsule including a taggant as disclosed herein.

FIG. 3 is a schematic drawing of capsule 300 which, in some embodiments, may be comprised of gelatin. Capsule 300 includes an outer surface 310 and an inner surface 320. Taggant layer 330 is disposed between outer surface 310 and inner surface 320. Taggant layer 330 is impregnated with a taggant. In some embodiments, taggant layer 330 comprises gelatin or another material used to manufacture capsule 300. The taggant may be mixed with the capsule material to incorporate taggant throughout taggant layer 330. Inner surface 320 and outer surface 310 may be disposed on either side of taggant layer 330 using a variety of manufacturing techniques. Inner surface 320 defines hollow space 340 into which the pharmaceutical or nutritional product may be placed. Consequently, inner surface 320 is between the pharmaceutical or nutritional product housed in hollow space 340 and the taggant in taggant layer 330. Any unwanted interaction between the taggant and the pharmaceutical or nutritional product is prevented. Outer surface 310 protects taggant layer 330 from the external environment so that no taggant is scraped off or destroyed before the subject consumes capsule 300. A blown up drawing of the area within the dashed circle is shown at the bottom of FIG. 3 for added clarity.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

What is claimed is:

1. A method of tracking consumption of a pharmaceutical product comprising the steps of:
   providing a subject with a pharmaceutical product, wherein the pharmaceutical product has been tagged with asparagusic acid;
   instructing the subject to consume the pharmaceutical product according to a defined protocol;
   collecting a sample of bodily waste from the subject; and
   analyzing the sample of bodily waste to detect the asparagusic acid or a metabolite thereof.

2. The method of claim 1, wherein the step of collecting a sample of bodily waste comprises collecting a volume of urine.

3. The method of claim 2, wherein the volume of urine comprises a 24-hour urine collection.

4. The method of claim 2, wherein the step of analyzing the sample of bodily waste comprises detecting the asparagusic acid or the metabolite thereof in a headspace above the volume of urine.

5. The method of claim 4, wherein the step of analyzing the sample of bodily waste is conducted using at least one of the following techniques: head space gas chromatography-mass spectrometry, head space gas chromatography-differential mobility spectrometry, and electronic nose analysis.

6. The method of claim 1, wherein the pharmaceutical product is provided within a capsule, and wherein the asparagusic acid or a metabolite thereof is impregnated within a material from which the capsule was constructed.

7. A method of tracking consumption of a pharmaceutical product comprising the steps of:
   providing a subject with a pharmaceutical product, wherein the pharmaceutical product has been tagged with garlic or an extract thereof;
   instructing the subject to consume the pharmaceutical product according to a defined protocol;
   collecting a sample of bodily waste from the subject using a toilet;
   analyzing the sample of bodily waste to detect allyl methyl sulfide; and
   assessing the subject's compliance based on the results of the analysis.

8. The method of claim 7, wherein the step of collecting a sample of bodily waste comprises collecting a volume of urine.

9. The method of claim 8, wherein the volume of urine comprises a 24-hour urine collection.

10. The method of claim 8, wherein the step of analyzing the sample of bodily waste comprises detecting allyl methyl sulfide in a headspace above the volume of urine.

11. The method of claim 10, wherein the step of analyzing the sample of bodily waste is conducted using at least one of the following techniques: head space gas chromatography-mass spectrometry, head space gas chromatography-differential mobility spectrometry, and electronic nose analysis.

12. The method of claim 7, wherein the pharmaceutical product is provided within a capsule, and wherein the garlic or the extract thereof is impregnated within a material from which the capsule was constructed.

13. A method of tracking consumption of a pharmaceutical product comprising the steps of:
   providing a subject with a pharmaceutical product, wherein the pharmaceutical product has been tagged with 1,8-cineole;
   instructing the subject to consume the pharmaceutical product according to a defined protocol;
   collecting a sample of bodily waste from the subject; and
   analyzing the sample of bodily waste to detect 2-hydroxycineole.

14. The method of claim 13, wherein the step of collecting a sample of bodily waste comprises collecting a volume of urine.

15. The method of claim 14, wherein the step of analyzing the sample of bodily waste comprises detecting 2-hydroxycineole in a headspace above the volume of urine.

16. The method of claim 15, wherein the step of analyzing the sample of bodily waste is conducted using liquid chromatography with tandem mass spectrometry.

17. The method of claim 16, in which the step of analyzing the sample of bodily waste is conducted within a toilet.

18. The method of claim 13, wherein the pharmaceutical product is provided within a capsule, and wherein the 1,8-cineole is impregnated within a material from which the capsule was constructed.

19. The method of claim 18, wherein the capsule comprises an inner surface and an outer surface, wherein the 1,8-cineole is disposed between the inner surface and the outer surface.

20. The method of claim 7 wherein the defined protocol comprises one or more of the timing of consumption, method of consumption, and consumption of other substances.

21. The method of claim 20 wherein the other substances comprise food.

22. The method of claim 20 wherein the method of consumption comprises taking the product orally, intranasally, intramuscularly, sublingually, or topically.

\* \* \* \* \*